US00PP14467P39

(12) United States Plant Patent
Moser

(10) Patent No.: US PP14,467 P3
(45) Date of Patent: Jan. 20, 2004

(54) CHRYSANTHEMUM PLANT NAMED 'MOZA RT 01'

(50) Latin Name: *Chrysanthemum morifolium*
Varietal Denomination: Moza RT 01

(75) Inventor: Frank Moser, Alva, FL (US)

(73) Assignee: Mozant, LLC, Oxnard, CA (US)

( * ) Notice: Subject to any disclaimer, the term of this patent is extended or adjusted under 35 U.S.C. 154(b) by 21 days.

(21) Appl. No.: 09/865,147

(22) Filed: May 24, 2001

(65) Prior Publication Data

US 2002/0188985 P1 Dec. 12, 2002

(51) Int. Cl.[7] ..... A01H 5/00
(52) U.S. Cl. ..... Plt./298
(58) Field of Search ..... Plt./298

(56) References Cited

U.S. PATENT DOCUMENTS

PP5,414 P * 3/1985 Duffett ..... Plt./298

* cited by examiner

*Primary Examiner*—Bruce R. Campell
*Assistant Examiner*—Anne Marie Grünberg
(74) *Attorney, Agent, or Firm*—Knobbe, Martens, Olson & Bear, LLP

(57) ABSTRACT

A new and distinct Chrysanthemum plant cultivar characterized by a daisy type inflorescence, a consistent flowering response to short days, blooming consistently after 45 days of short day length, a free branching habit, a consistent natural season flowering habit during the first two weeks of September, and dark purple/red ray florets.

1 Drawing Sheet

LATIN NAME OF THE GENUS AND SPECIES OF THE PLANT CLAIMED
*Chrysanthemum morifolium.*
VARIETY DENOMINATION
'MOZA RT 01'.

BACKGROUND OF THE INVENTION

The present invention relates to a new and distinct cultivar of Chrysanthemum plant, herein after referred to by the cultivar name 'MOZA RT 01.'

The new cultivar is a product of induced mutation by radiation. The new cultivar originated by exposing an entire plant of the Chrysanthemum cultivar 'MZT TMP8' (U.S. Plant Pat. No. 11,866) to radiation. This cultivar was discovered and selected by the inventor in November 1998.

Asexual reproduction of the new cultivar by apical tip cutting and meristem tissue culture was performed in Oxnard, Calif. and has shown that the unique features of this cultivar are stable and reproduced true to type on successive generations.

SUMMARY OF THE INVENTION

The cultivar 'MOZA RT 01' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'MOZA RT 01.' These characteristics in combination distinguish 'MOZA RT 01' as a new and distinct Chrysanthemum cultivar:

1. Daisy type inflorescence;

2. Consistent flowering response to short days, blooming consistently after 45 days of short day length;

3. Free branching habit;

4. Consistent natural season flowering habit during the first two weeks of September; and 5. Dark purple/red ray florets.

Plants of the new cultivar are similar to plants of the parent cultivar, 'MZT TMP8' in most horticultural characteristics, however plants of the new cultivar differed from plants of the cultivar 'MZT TMP8' primarily in ray floret color, number of ray florets, and number of disc florets. The new cultivar 'MOZA RT 01' has darker, more reddish purple ray florets than the parent cultivar. The new cultivar has fewer ray florets than the parent cultivar, with an average of 80 florets compared to the parent's 110 florets, in similar cultural conditions. The new cultivar also has more disc florets than the parent.

BRIEF DESCRIPTION OF THE PHOTOGRAPHS

The photograph shows a plant of the new cultivar which was grown in a 2-gallon container. A single cutting was grown in the container, and the plant was grown in outdoor field conditions.

DETAILED BOTANICAL DESCRIPTION

In the following description, color references are made to The Royal Horticultural Society Colour Chart except where general terms of ordinary dictionary significance are used. The following observations and measurements describe approximately 75 day old plants grown in a commercial field in Oxnard, Calif. during the month of September 2000. The plants were grown from a rooted cutting given one pinch after 10 days from planting. There was no spray or disbud treatment given. The growing temperature ranged from 60° to 65° F. at night to 70° to 85° F. during the day. Measurements and numerical values represent averages of typical flowering types.

Botanical classification: *Chrysanthemum morifolium* cultivar 'MOZA RT 01'.
Commercial classification: Garden-type Chrysanthemum.
Parentage: Induced mutation of *Chrysanthemum morifolium* cultivar 'MZT TMP8'.
Comparison to siblings: The results of the mutation were found to be random, with most siblings producing ray florets of similar color to the parent variety. Additionally, blooming response varied in the sibling population from 45 days to 55 days. Many siblings produced were shorter than the selected new variety. MOZA RT 01 was the only prodigy producing reddish ray florets with a 45 day blooming response of consistent size, as described herein.
Comparison Variety: GEDI RT U.S. Plant Pat. No. 11,236.

The new variety differs from GEDI RT in having more ray florets, more disc florets and an earlier natural season blooming response.

PROPAGATION

Time to rooting: 7 to 14 days at approximately 21° C.
Rooting habit: Fine, fibrous.

PLANT

Growth habit: Mounding herbaceous perennial.
Height: Approximately 25 cm.
Branching characteristics: Free Branching.
Internode length: Approximately 2.4 cm.

FOLIAGE

Leaf:
- *Arrangement*.—Alternate single.
- *Average length*.—Approximately 6.5 cm.
- *Average width*.—Approximately 3.5 cm.
- *Shape of blade*.—Ovate.
- *Apex*.—Acuminate.
- *Base*.—Attenuate.
- *Attachment*.—Stalked.
- *Margin*.—Serrate.
- *Texture of top surface*.—Lightly pubescent.
- *Texture of bottom surface*.—Lightly pubescent.
- *Color*.—Young foliage upper side: Near 137A. Young foliage under side: Near 137B. Mature foliage upper side: Near 137A. Mature foliage under side: Near 137B. Venation upper side: Near 137C. Venation under side: Near 137D.

Petiole:
- *Average length*.—Approximately 2.0 cm.
- *Petiole color*.—Approximately 137A.

BLOOM

Inflorescence:
- *Flowering habit*.—Induced by darkness period greater than 13.5 hours, consistently blooms after 45 days of appropriate day length.
- *Inflorescence form*.—Daisy.
- *Natural flowering season*.—Approximately the first two weeks of September.
- *Number of inflorescences per stem*.—Approximately 9.
- *Inflorescence diameter*.—Approximately 4.5 cm.
- *Inflorescence depth*.—1.5 cm.
- *Disc diameter*.—1.5 cm.
- *Inflorescence longevity on plant*.—Approximately 18–22 days.
- *Persistence*.—Persistent.
- *Fragrance*.—Not present.

Ray florets:
- *Appearance*.—Matte.
- *Texture*.—Smooth.
- *Average number per flower*.—Approximately 80.
- *Shape*.—Oblanceolate.
- *Margin*.—Entire.
- *Apex*.—Obtuse.
- *Length*.—Approximately 2.0 cm.
- *Width*.—Approximately 0.5 cm.
- *Color*.—Upper surface at first opening: Near 59A. Upper surface at maturity: Near 59D. Upper surface at fading: Near 60A. Under surface at first opening: Near 79A. Under surface at maturity: Near 70B. Under surface at fading: Near 70B.

Disc florets:
- *Appearance*.—Shiny.
- *Texture*.—Smooth.
- *Average number per flower*.—Approximately 200.
- *Shape*.—Cylindric.
- *Apex*.—Obtuse.
- *Average length*.—Approximately 0.7 cm.
- *Average width*.—Approximately 0.1 cm.
- *Color*.—At first opening: Near 16A. At maturity: Near 16A. At fading: Near 22A.

Peduncle:
- *Length*.—At terminal end (shortest): Approximately 4 cm. At lateral end (longest): Approximately 6 cm.
- *Strength*.—Moderate.
- *Color*.—137C.
- *Habit*.—Erect.

Inflorescence bud:
- *Length*.—Approximately 0.8 cm.
- *Diameter*.—Approximately 0.8 cm.
- *Form*.—Globular.
- *Color*.—Near 138A.

Sepals:
- *Appearance*.—Matte.
- *Texture*.—Lightly pubescent.
- *Number*.—Approximately 30 to 40.
- *Shape*.—Ovate.
- *Margin*.—Entire.
- *Apex*.—Acute.
- *Color*.—Upper side: Near 137B. Under side: Near 137B.

REPRODUCTIVE ORGANS

Ray florets:
- *Number of pistils per floret*.—1.
- *Stigma shape*.—2 branched.
- *Stigma color*.—Near 7D.
- *Stigma length*.—0.6 cm.
- *Style color*.—Near 7D.
- *Number of stamens per floret*.—Absent.

Disc florets:
- *Number of pistils per floret*.—1.
- *Stigma shape*.—Cylindric.
- *Stigma color*.—Approximately 2C.
- *Style length*.—0.5 cm.
- *Style color*.—Approximately 154A.
- *Number of stamens per floret*.—Approximately 5.
- *Anther shape*.—Tubular.
- *Anther color*.—Near 14C.
- *Pollen color*.—Near 15A.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests have been observed in this cultivar.

What is claimed is:

1. A new and distinct cultivar of Chrysanthemum plant named 'MOZA RT 01' as herein illustrated and described.

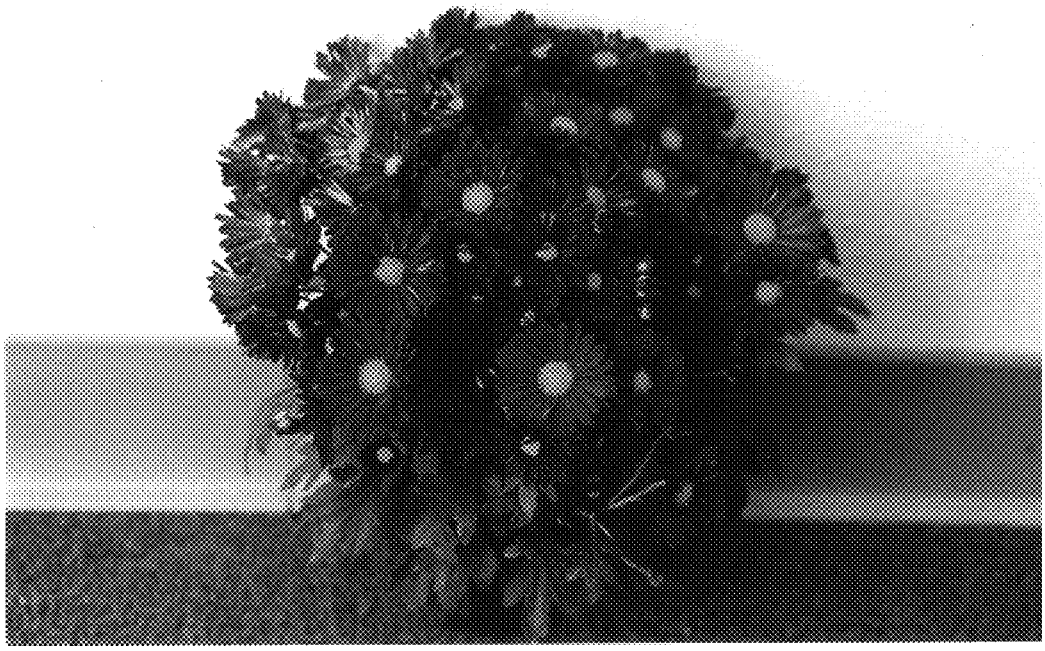

* * * * *